United States Patent [19]
Clawson

[11] Patent Number: 6,010,451
[45] Date of Patent: *Jan. 4, 2000

[54] METHOD AND SYSTEM FOR GIVING REMOTE EMERGENCY MEDICAL COUNSEL TO CHOKING PATIENTS

[76] Inventor: Jeffrey J. Clawson, 4649 Farm Meadow La., Salt Lake City, Utah

[*] Notice: This patent issued on a continued prosecution application filed under 37 CFR 1.53(d), and is subject to the twenty year patent term provisions of 35 U.S.C. 154(a)(2).

[21] Appl. No.: 08/832,616

[22] Filed: Mar. 28, 1997

Related U.S. Application Data

[60] Provisional application No. 60/014,741, Mar. 29, 1996.

[51] Int. Cl.[7] .................................................. A61B 5/08
[52] U.S. Cl. ........................... 600/300; 600/529; 128/920
[58] Field of Search ..................................... 128/920, 923, 128/924, 903, 904, 905; 600/408, 300, 529; 364/922, 922.2, 922.3, 922.4

[56] References Cited

U.S. PATENT DOCUMENTS

| | | | |
|---|---|---|---|
| 4,130,881 | 12/1978 | Haessler et al. | 364/900 |
| 4,237,344 | 12/1980 | Moore | 179/2 A |
| 4,290,114 | 9/1981 | Sinay | 364/900 |
| 4,489,387 | 12/1984 | Lamb et al. | 364/514 |
| 4,731,725 | 3/1988 | Suto et al. | 364/415 |
| 4,839,822 | 6/1989 | Dormond et al. | 364/513 |
| 4,858,121 | 8/1989 | Barber et al. | 364/406 |
| 4,945,476 | 7/1990 | Bodick et al. | 364/413.02 |
| 5,063,522 | 11/1991 | Winters | 395/51 |
| 5,065,315 | 11/1991 | Garcia | 364/413.01 |
| 5,072,383 | 12/1991 | Brimm et al. | 364/413.02 |
| 5,086,391 | 2/1992 | Chambers | 364/413.02 |
| 5,228,449 | 7/1993 | Christ et al. | 128/691 |
| 5,253,164 | 10/1993 | Holloway et al. | 364/406 |
| 5,255,187 | 10/1993 | Sorensen | 364/413.02 |
| 5,404,292 | 4/1995 | Hendrickson | 364/413.02 |
| 5,462,051 | 10/1995 | Oka et al. | 128/630 |
| 5,471,382 | 11/1995 | Tallman et al. | 364/406 |
| 5,521,812 | 5/1996 | Feder et al. | 364/400 |
| 5,544,649 | 8/1996 | David et al. | 128/630 |
| 5,594,638 | 1/1997 | Iliff | 395/203 |
| 5,596,994 | 1/1997 | Bro | 128/732 |
| 5,660,176 | 8/1997 | Iliff | 128/630 |

*Primary Examiner*—Francis J. Jaworski
*Attorney, Agent, or Firm*—Lloyd W. Sadler

[57] ABSTRACT

A method and system for providing emergency medical counseling to choking patients remotely is described. A consistent, standard and systematic process is provided which in combination with adequate training, supervision and quality assurance serves to provide a method for gathering emergency medical information regarding providing emergency medical dispatch services to choking victims, categorizing such information into various determinant levels for appropriate response, and for giving qualified emergency medical information to callers thereby permitting "zero time" response by those at the scene. By using this invention properly a dispatcher is guided through the interrogation of callers concerned with choking victims injuries, gathering critical information and giving the appropriate guidance to the caller. This invention specifically guides the dispatcher through the steps of the procedure for giving remote emergency medical counsel to choking victims, thereby providing the "zero time" response by utilizing those at the scene of the emergency.

4 Claims, 20 Drawing Sheets

Within ProQA, during the initial case entry, the user is allowed to enter one of three values for the patient's state of consciousness and one of four values for their breathing status. Based on these two parameters, one of four possible lists should be displayed to limit the user's selection of the final data entry field.

The following is a truth table for the input and output values of the formula:

| Conscious | Breathing | Chief Complaint list |
|---|---|---|
| No | Yes | 31, 9, 11, 12, 13, 14, 15, 23, any other card |
| No | No | 9, 11, 14, 15, any other card |
| No | Unknown | 9, 11, 14, 15, any other card |
| No | Uncertain | 9, 11, 14, 15, any other card |
| Yes | Yes | Any card |
| Yes | No | 11 |
| Yes | Unknown | Any card |
| Yes | Uncertain | 11 |
| Unknown | Yes | Any card |
| Unknown | No | 9, 11, 14, 15, any other card |
| Unknown | Unknown | Any card |
| Unknown | Uncertain | 9, 11, 14, 15, any other card |

The following is a function, written in the C programming language (copyright 1996 by Medical Priority Consultants, Inc.), that implements the above table.

```c
// Input values for conscious parameter
#define CONS_NO    0
#define CONS_YES   1
#define CONS_UNK   2

// Input values for breathing parameter
#define BRTH_NO    0
#define BRTH_YES   1
#define BRTH_UNK   2
#define BRTH_UNC   3

// Output values for valid_cc function
#define CCS_ALL    0    // Choice of chief complaints: any
#define CCS_HPLUS  1    // Choice of chief complaints: 31, 9, 11, 12, 13, 14, 15, 23, any other
#define CCS_HEART  2    // Choice of chief complaints: 9, 11, 14, 15, any other
#define CCS_CHOK   3    // Choice of chief complaints: 11

// Determine the chief complaint codes valid for the conscious and breathing responses entered
int valid_cc(int conscious, int breathing)
{
   switch (conscious)
     {
      case CONS_NO:
        switch (breathing)
          {
           case BRTH_YES:   return (CCS_HPLUS);

case BRTH_NO:
           case BRTH_UNK:
           case BRTH_UNC:   return (CCS_HEART);
          }
        break;
      case CONS_YES:
        switch (breathing)
          {
           case BRTH_YES:
           case BRTH_UNK:   return (CCS_ALL);

case BRTH_UNC:
           case BRTH_NO:    return (CCS_CHOK);
          }
        break;
      case CONS_UNK:
        switch (breathing)
          {
           case BRTH_YES:
           case BRTH_UNK:   return (CCS_ALL);

case BRTH_NO:
           case BRTH_UNC:   return (CCS_HEART);
          }
        break;
     }
   return (CCS_ALL);
}
```

FIG. 8i

Database Locations:

| Id | Location | Description |
|----|----------|-------------|
| 1 | :AMPDS: | Main directory for AMPDS database. |
| 2 | :PROQA1: | Directory for files that are specific to ProQA. |
| 3 | :CARDS: | Directory for files that are specific to Cards. |
| 4 | :AMPDS_QA: | "Quality Assurance" directory. Current holds tables that are used by translators. |
| 5 | :AMPDS_SEC: | Directory for tables containing passwords and security rights for the users of the |
| 6 | :CARD_RPT: | Directory for Card reports. |
| 7 | :GUIDocumenter: | Directory for the GUI Documenter application that is (among other things) used for |
| 8 | :MPC_RSC: | General database containing MPC resources. AMPDS is using the EMP.DB |
| 9 | :PROQA_RPT: | Directory for ProQA reports. |
| 10 | p:\delphi\expproqa | Location of the ProQA Export Program. |
| 11 | p:\delphi\protocol | Location of the Protocol maintenance program. |
| 12 | :Tools: | Location of character set translation tables and Paradox progress bar. |

Database Tables:

| Table Name | Loc | Long Name | Description |
|------------|-----|-----------|-------------|
| AI-ELEM.DB | 1 | Additional Information Element | Each element in a AI section list. |
| AI-PTYP.DB | 1 | Additional Information Paragraph Type | |
| AI-SECT.DB | 1 | Additional Information Section | Section of additional information with title, sub-titles, and |
| AI.DB | 1 | Additional Information | Link between AI-SECT and CHIEFCOM |
| AISECTYP.DB | 1 | Additional Information Section Type | Normal, multi-column, rule, axiom |
| ATTRIBUT.DB | 1 | Attributes | List of valid attributes to use in text styles |
| CARDCHG.DB | 1 | Card Changes | List of upcoming changes to the AMPDS Cards. These changes may |
| CHIEFCOM.DB | 1 | Chief Complaints | |
| ELEMUSE.DB | 1 | Element Usage | Shows in which tables elements are used |
| FNTCOLOR.DB | 1 | Font Color | ObjectPal Color Constants and names |
| FONTATTR.DB | 1 | Font Attribute | ObjectPal Font (style) Constants and names |
| FONTS.DB | 1 | Fonts | List of fonts available in Windows |
| GENDER.DB | 1 | Gender | Lookup table for gender expression: masculin, feminin, |
| GENDNDX.DB | 1 | Gender Index | Index showing in which text elements a certain gender expression |
| KEYQUEST.DB | 1 | Key Questions | Question Pool |
| KQ-RESP.DB | 1 | Key Question Response | Question Pool Answers |
| KQR-HLIT.DB | 1 | Key Question Response Highlight | Highligh characters for answers |
| KQR-TRIG.DB | 1 | Key Question Response Trigger | Auto-answer list |
| LANGLINK.DB | 1 | Language Link | Link between a text string and Language. (One text string can be |
| LANGUAGE.DB | 1 | Language | List of languages supported |
| LISTDEF.DB | 1 | List Definitions | Detail Table to LISTTYPE |
| LISTTYPE.DB | 1 | List Types | Used by the ProQA/Card export programs |
| LOGICDOC.DB | 1 | Logic Documentation | General documentation of the protocol logic |
| MN-AMPDS.DB | 1 | Menu AMPDS | The menu system loaded by the "Welcome" form |
| MNREPORT.DB | 1 | Menu Report | Used when printing AMPDS Menu System. |
| NEW-CC.DB | 1 | New Chief Complaint | Shunt from one CC to another |
| NEW-PAI.DB | 1 | New PAI | Shunt from one CC to a PAI |
| PAI-CARD.DB | 1 | PAI Cards | List of PAI cards: A, B, C, D, E, F, G, H |
| PAI-NOTE.DB | 1 | PAI Footnotes | Now called "Special Instructions" for pre-arrival instructions (PAI) |
| PAI-RESP.DB | 1 | PAI Responses | Answer for PAI question |
| PAI-STEP.DB | 1 | PAI Step | Each PAI box is split into steps where each step usually is one |
| PAI.DB | 1 | PAI | The list of all PAIs - one record for each box on the cards + additional |
| PAIRHLIT.DB | 1 | PAI Response Highlight Characters | Highlight/activation/accelerator keys for PAI answer boxes |
| PDI.DB | 1 | Post-dispatch Instructions | |

FIG. 8j

| Table Name | Loc | Long Name | Description |
|---|---|---|---|
| PROQACOL.DB | 1 | ProQA Colors | ProQA color constants |
| PROTAREA.DB | 1 | Protocol Area | Describes unique "areas" of the protocol like Key Questions, PAI, PDI |
| PROTCLAS.DB | 1 | Protocol Class | Categorization of text: normal, highlight, reference words, operator |
| Q-FOR-CC.DB | 1 | Questions For Chief Complaint | Which questions are used on which card/complaint |
| STYLEMAP.DB | 1 | Style Map | Defines which "styles" to use when exporting protocol classes in the |
| TEXT.DB | 1 | Text | All text strings for all languages are stored in this table |
| TTSLOG.DB | 1 | Transaction Tracking System Log | All changes in the database should be logged to this table (Not Determinants) |
| DISPPRI.DB | 2 | Dispatch Priority | |
| DP-CR-AN.DB | 2 | Dispatch Priorities Criteria Answers | Can also be described as the "AND" level of the logic. |
| DP-CRIT.DB | 2 | Dispatch Priorities Criteria | Can also be described as the "OR" level of the logic. |
| EXPRTLOG.DB | 2 | Export log (ProQA) | Log for exports (ProQA Export Form) |
| PP-LINE.DB | 2 | Program Text Lines | Program Text for ProQA |
| PP-PROG.DB | 2 | Program Text Programs | Program Text for ProQA |
| PP-SECT.DB | 2 | Program Text Sections | Program Text for ProQA |
| PREVQ.DB | 2 | Previous Questions | Previous question requirement in question list |
| PREVQLST.DB | 2 | Previous Question List | Previous question requirement in question list |
| PROQADEF.DB | 2 | ProQA Definitions | Constant definitions used by export programs |
| PROQAVER.DB | 2 | ProQA Version | Binary file header information (ProQA Export program) |
| CE-ANS.DB | 3 | Case Entry Answers | Case Entry Protocol Card. Answers for questions. |
| CE-CARD.DB | 3 | Case Entry Card | Elements for export to Case Entry Card (Protocol). |
| CE-QUEST.DB | 3 | Case Entry Questions | Case Entry Protocol questions. |
| EXPRTLOG.DB | 3 | Export log (Cards) | |
| KQ-GOTO.DB | 3 | Key Question Go To | |
| QRK-TPL.DB | 3 | Quark Templates | |
| WORKELEM.DB | 3 | Work Elements | Used by Quark Export? |
| QA-APP.DB | 4 | Quality Assurance Application | |
| QA-DBITM.DB | 4 | Quality Assurance DB Item | |
| QA-ISSUE.DB | 4 | Quality Assurance Issue | |
| QA-ISTAT.DB | 4 | Quality Assurance Issue Status | |
| QA-STAFF.DB | 4 | Quality Assurance Staff | This table should be phased out and replaced by the |
| QA-TEXT.DB | 4 | Quality Assurance Text | |
| QA-TXSTA.DB | 4 | Quality Assurance Text Status | Not currently used, but is referenced in the QA forms. |
| SEC-CODE.DB | 5 | Security Codes | |
| USER.DB | 5 | User | |
| RPTSTYLE.DB | 6 | Report Styles | |
| ACCEL.DB | 7 | Accelerator Keys | Accelerator keys for ProQA menus. Except are Key Question Short |
| MENULOG.DB | 7 | Menu Log | |
| OUTLINE.DB | 7 | Outline | Main table for the GUI Documenter/Menu Edit program. This table |
| TEXTLIST.DB | 7 | Text List | |
| EMP.DB | 8 | Employees | |
| AI-ELEM.DB | 9 | Additional Information Elements (Rep( | |
| AI-SECT.DB | 9 | Additional Information Section (Report | |
| CCLSTRSP.DB | 9 | Chief Complaint List Responses (Rep | |
| CHIEFCOM.DB | 9 | Chief Complaints (Reports) | |
| DISPPRI.DB | 9 | Dispatch Priority (Reports) | |
| DP-CR-AN.DB | 9 | Dispatch Priorities Criteria Answers (F | |
| KEYQUEST.DB | 9 | Key Questions (Reports) | |
| KQ-DTAIL.DB | 9 | Key Question Details (Reports) | |
| KQ-RESP.DB | 9 | Key Question Response (Reports) | |
| KQD-RESP.DB | 9 | Key Question Detail Response (Repor | |
| KQR-SIMI.DB | 9 | Key Question Response - Similar Ans | |
| PAI-CARD.DB | 9 | PAI Cards (Reports) | |
| PAI-NOTE.DB | 9 | PAI Footnotes (Reports) | |
| PAI-RESP.DB | 9 | PAI Responses (Reports) | |
| PAI.DB | 9 | PAI (Reports) | |

FIG. 8k-1

| Table Name | Loc | Long Name | Description |
|---|---|---|---|
| PDI.DB | 9 | Post-dispatch Instructions | |
| CHARSET.DB | 12 | Character Set | Table for conversion between Windows, DOS, and Macintosh |

FIG. 8k-2

1 Abdominal Pain/Problems – CHIEF COMPLAINT

WHAT USER SEES:

QUESTIONS:

|   |   |   |   |
|---|---|---|---|
| 1 | {does} {he} have chest pain also? | Q122 | 1050121 |
| 2 | {is} {he} alert *(able to talk)*? | Q5 | 1050004 |
| 3 | Has she fainted? | Q207 | 1050005 |

DETERMINANTS

|   |   |   |
|---|---|---|
| A1 | Abdominal pain | 1010045 |
| C1 | Males *(age => 35)* | 1040001 |
| C2 | Females *(age => 45)* | 1040002 |
| C3 | Not alert | 1040003 |
| C4 | Females with fainting *(age 12-50)* | 1040004 |

FIG. 8l

| Kq# | Question |
|---|---|
| 1 | Is the patient male or female? |
| 2 | {is} {he} conscious |
| 3 | {is} {he} breathing? |
| 4 | {does} {he} have chest pain? |
| 5 | {is} {he} alert *(able to talk)*? |
| 6 | Has she fainted? |
| 7 | {does} {he} have difficulty breathing or swallowing? |
| 8 | Do you know exactly where {he} {is}? |
| 9 | {does} {he} have a rash, hives, or itching? |
| 10 | When did this start? |
| 11 | {does} {he} have a history of allergies? |
| 12 | What kind of animal is it? |
| 13 | Where is the animal now? |
| 14 | Where {was} {he} bitten *(what part of the body)*? |
| 15 | Is there any serious bleeding? |
| 16 | What type of complaint is this? |
| 17 | When did this happen? |
| 18 | Is the assailant *(attacker)* still nearby? |
| 19 | {is} {he} breathing normally? |
| 20 | *(If not obvious)* What part of the body was injured? |
| 21 | Are there any other injuries? |
| 22 | Is there any serious bleeding? |
| 23 | When did this happen *(start)*? |
| 24 | What caused the back pain? |
| 25 | Did {he} faint *(pass out)*? |
| 26 | {is} {he} choking? |
| 27 | {is} {he} sweaty or changing color? |
| 28 | {does} {he} have any heart problems? |
| 29 | {does} {he} have asthma? |
| 30 | How {was} {he} burned *(or injured)*? |
| 31 | *(If suspected)* Is anything *(structure)* still burning? |
| 32 | {is} {he} safe and out of danger? |
| 33 | {does} {he} have difficulty breathing? |
| 34 | What areas of {his} {body} are burned? |
| 35 | {is} {he} alert and able to talk? |
| 36 | {is} {he} burned? |
| 37 | {is} {he} contaminated with chemicals? |
| 38 | What kind of fumes are they? |
| 39 | Where are the fumes *(chemicals)* coming from? |
| 40 | Tell me what happened. |
| 41 | Did {he} choke on anything first? |
| 42 | Tell me why do you think {he's} dead? |
| 43 | Where exactly is the pain? |
| 44 | Is it sharp *(stabbing)*, or dull *(pressure)*? |
| 45 | *(If suspected)* Did {he} take any drugs *(medications)* in the past 12hrs? |
| 46 | {is} {he} still choking? |
| 47 | {is} {he} able to talk or cough? |
| 48 | Can {he} breathe at all? |
| 49 | What did {he} choke on? |
| 50 | {does} {he} have a history of heart problems? |
| 51 | Did {he} hit {his} head before the seizure? |
| 52 | Is she pregnant? |
| 53 | {is} {he} diabetic? |
| 54 | {has} {he} had more than one seizure now? |
| 55 | {is} {he} an {epileptic} or ever had a seizure before? |
| 56 | Has the jerking *(twitching)* stopped yet? |
| 57 | {is} {he} breathing now? |
| 58 | {does} {he} take insulin? |

FIG. 8m

| Q1 | Is the patient male or female? | | | 1050000 |
|---|---|---|---|---|
| Answers: | | | | |
| 1 | Male | 1060000 | The patient is male. | 1070000 |
| 2 | Female | 1060001 | The patient is female. | 1070001 |
| 3 | Unknown | 1060002 | The gender is not known. | 1070002 |

| Q2 | {is} {he} conscious | | | 1050001 |
|---|---|---|---|---|
| Answers: | | | | |
| 1 | Yes | 1060006 | Conscious.<br>198-2 AUTO ANSWER | 1070003 |
| 2 | No | 1060004 | Unconscious.<br>5-2   35-2   120-2   129-2   145-2   176-3   189-2 | 1070004 |
| 3 | Unknown | 1060002 | Consciousness unknown.<br>5-3 | 1070005 |

| Q3 | {is} {he} breathing? | | | 1050002 |
|---|---|---|---|---|
| Answers: | | | | |
| 1 | Yes | 1060006 | Patient is breathing. | 1070006 |
| 2 | No | 1060004 | Patient is not breathing.<br>7-5   19-2   164-5 | 1070007 |
| 3 | Uncertain | 1060008 | Breathing is uncertain.<br>19-3 | 1070008 |
| 4 | Unknown | 1060002 | Breathing is unknown.<br>19-3 | 1070009 |

| Q4 | {does} {he} have chest pain? | | | 1050003 |
|---|---|---|---|---|
| Answers: | | | | |
| 1 | Yes | 1060006 | {he} {has} chest pain.<br>122-2 | 1070010 |
| 2 | No | 1060004 | {he} {does} not have chest pain.<br>122-1 | 1070011 |
| 3 | Unknown | 1060002 | It is not known if {he} {has} chest pain.<br>122-3 | 1070012 |

*Asked by Chief Complaints:*

19  Heart Problems
20  Heat/Cold Exposure
26  Sick Person (Specific Diagnosis)
  *Question is available if:*
  Patient is older than 34

| Q5 | {is} {he} alert (able to talk)? | 1050004 |
|---|---|---|

FIG. 8n

1  Abdominal Pain/Problems

1   Q122 {does} {he} have chest pain also?                                    1050121

NOT PQ3 A2

A1    {he} {does} not have chest pain.
    A2    {he} {has} chest pain.                                       GOTO CC-10
    A3    It is not known if {he} {has} chest pain.

*Patient is older than 34*
    *Show Additional Information*

2   Q5 {is} {he} alert *(able to talk)*?                                       1050004

NOT PQ3 A2

A1    {he} {is} alert.
    A2    {he} {is} not alert.
    A3    It's not known if {he} {is} alert.

3   Q207 Has she fainted?                                                       1050005

NOT PQ1 A1     NOT PQ3 A2

A1    {he} {has} fainted.
    A2    {he} {has} not fainted.
    A3    {he} had a near fainting episode.
    A4    It is not known if {he} fainted.

*Patient is older than 11*
    *Patient is younger than 51*

FIG. 8o

| | | |
|---|---|---|
| 1 | Abdominal Pain/Problems | 1020000 |
| A1 | Abdominal pain | 1010045 |

| | |
|---|---|
| 1 | Default |

| | | |
|---|---|---|
| C1 | Males (age => 35) | 1040001 |

| | | |
|---|---|---|
| 1 | Age > 34 | |
| | NOT 1-2 | The patient is female. |
| | NOT 5-0 | OK if Question not answered yet! |
| | NOT 5-2 | {he} {is} not alert. |
| | NOT 207-1 | {he} {has} fainted. |
| | NOT 207-3 | {he} had a near fainting episode. |

| | | |
|---|---|---|
| C2 | Females (age => 45) | 1040002 |

| | | |
|---|---|---|
| 1 | Age > 44 | |
| | 1-2 | The patient is female. |
| | NOT 5-0 | OK if Question not answered yet! |
| | NOT 5-2 | {he} {is} not alert. |
| | NOT 207-1 | {he} {has} fainted. |
| | NOT 207-3 | {he} had a near fainting episode. |

| | | |
|---|---|---|
| C3 | Not alert | 1040003 |

| | | |
|---|---|---|
| 1 | | |
| | 5-2 | {he} {is} not alert. |
| 2 | Unknown Consciousness | |
| | 5-3 | It's not known if {he} {is} alert. |
| 3 | Not Breathing | |
| 4 | | |
| | NOT 2-1 | Conscious. |
| | NOT 3-1 | Patient is breathing. |
| 5 | | |
| | NOT 3-1 | Patient is breathing. |
| | NOT 5-0 | OK if Question not answered yet! |
| | NOT 5-1 | {he} {is} alert. |
| 6 | | |
| | NOT 2-1 | Conscious. |
| | NOT 5-0 | OK if Question not answered yet! |
| | NOT 5-1 | {he} {is} alert. |

| | | |
|---|---|---|
| C4 | Females with fainting (age 12-50) | 1040004 |

FIG. 8p

When To Recommend Dispatch:

Old Algorithm: FOR DISPATCHING
*Criteria 1:* When no more questions to ask.
*Criteria 2:* When a Delta is identified, and there is more than one question left to ask.
*Criteria 3:* When a Charlie is identified, and no Delta can possibly be identified, and there is more than one question left to ask.

Current Algorithm: FOR DISPATCHING
*Criteria 1:* When no more questions to ask.
*Criteria 2:* When a Delta is identified, and there is more than one question left to ask.
*Criteria 3:* When a Charlie is identified, there are no Deltas on the card, and there is more than one question left to ask.
*In other words, on a card with both Charlies and Deltas, continue to ask questions even if a Charlie is identified.*
*See Proof Sheet #1622 for Jeff's comments.*
*This was implemented on 4/5/95. TL.*

*Warning:* When deciding whether there are any Delta's that may be identified later, ProQA does not not look at questions that will be "auto-answered". This means that ProQA may make an incorrect decision if a Delta is dependant on a question that is not in the question list for this card, but will be auto-answered by one of the questions in the list.

Age and Gender Dependent Cards:

The following cards have questions that are age dependent: 1,5,10,12,21,23,26,31.
The following cards HAVE QUESTIONS THAT ARE GENDER DEPENDENT: 1,12,21,31.
The logic does now work correctly for unknown gender and/or age. The "Insufficient info..." dialog boxes are not used any more. On any age/gender dependent card, the logic takes a *"worst case"* scenario when age/gender is unknown.

Logic changes done to allow for unknown gender/age in chief complaints.

<u>CARD</u>  <u>CHANGE</u>
  1    a) Removed the upper age limit on question 1.
       b) Removed "Gender=female" (G2) from question 3, and added previous
          question criterium: ":P1-!1". This effectively changes the logic
          from asking the question if "gender is female", to asking the question
          if "gender is not male" (includes unknown gender).

5    No change.

10    No change - unknown age now will highlight both determinant A1 and C1,
       and will recommend C1.

12    a) No change in gender - question 2 "Is she pregnant?" will only be asked
          if gender is female. Implicitly, if gender is unknown, any pregnancy
          condition also is unknown.
       b) No changes in age - unknown now highlights both B1 and D2.

21    No change - same logic for gender as card 12 above.

23    No change - unknown age highlights both O1 and B1.

26    No change 31    a) Same as card 1 b).
       b) Added "not male" as a criteria for determinant C3.

FIG. 8q

The Question Pool Auto-answer Feature:

There is a possible problem with the auto-answer feature (example):
Q57 "Is he breathing now?" - answer 3 "Unknown" used to auto-answer Q141 "You go check - I'll stay on the line. Is he breathing now?" - answer 3 "Unknown". On chief complaint 12, Q141 is only being asked if Q57 is answered with "Unknown". The problem is that Q141 will not be asked in this case either because it has already been auto-answered. As a conclusion Q141 answer 3 should not be auto-answered by Q57 answer 3 in this case.

ProQA Colors:

Color Scheme:

| 0 | White | 4 | Cyan |
| 1 | Yellow | 5 | Red |
| 2 | Green | 6 | Magenta |
| 3 | Gray | 7 | Darkgray/Black |

Color of Question Numbers:

| Green | Driver (includes priority SK) |
| Yellow | Shunt KQ |
| Cyan | Info (not a driver) |
| Red | Safety |
| White | Verification and questions to EMD |

Other:

RELATIONSHIP BETWEEN CONSCIOUSNESS AND ALERTNESS:

| Alert | $\Rightarrow$ | Conscous |
| Unconscious | $\Rightarrow$ | Not Alert |
| Consciousness Unknown | $\Rightarrow$ | Alert Unknown |
| | | |
| Not Alert | $\neq$ | Unconscious |
| Alert Unknown | $\neq$ | Consciousness Unknown |
| Conscious | $\neq$ | Alert |

How to use the default flag in determinant logic:

The old logic on chief complaint 20 (and possibly on others) showed an example with two incorrect usages of the default flag (:D).

Error 1: The default flag was used on more than one determinant.
Error 2: The default flag was used in combination with another qualifier on the same line ("and" statement).

Currently, the logic only uses the last default flag found in the logic on a chief complaint. Also, currently, the logic ignores any other qualifiers on the same "and" line as a default flag. (TL, 9/12/95)

Omega Protocols:

Rule 1: Only select O-1 if there are no unknown factors.

FIG. 8r 6,010,451

METHOD AND SYSTEM FOR GIVING REMOTE EMERGENCY MEDICAL COUNSEL TO CHOKING PATIENTS

SPECIFICATION

To all whom it may concern:

Be it known that Jeffrey J. Clawson, a citizen of the United States of America, has invented a new and useful invention entitled METHOD AND SYSTEM FOR GIVING REMOTE EMERGENCY MEDICAL COUNSEL TO CHOKING PATIENTS of which the following comprises a complete specification. This application is based on Provisional Application Serial No. 60/014,741, which was filed on Mar. 29, 1996, and priority is claimed thereto.

SOFTWARE APPENDIX

This specification includes a software appendix which includes an enabling description of one preferred embodiment of the design and implementation of the process of the invention in the computer software alternative embodiment of the invention. This appendix is produced herein to provide programmers of ordinary skill in the arts of emergency medical procedures and computer programming all information necessary to enable their coding, use and practice of the software embodiment of the invention. In other embodiments of the invention, the inventive concept may be implemented in other computer code, in computer hardware, in other circuitry, in a combination of these, in a reference card or flowchart format not involving computer technology at all, or otherwise. An alternative preferred embodiment of the invention is a reference card format. The software appendix is hereby incorporated by reference in its entirety and is considered to be a part of the disclosure of this specification.

BACKGROUND OF THE INVENTION

1. Field of the Invention

This invention relates to methods and systems for processing and responding to emergency medical inquiries. Specifically, this invention relates to the process of providing emergency medical counsel, instruction or advice to callers who are inquiring concerning medical choking cases. Providing adequate emergency medical care presents several critical challenges to medical care providers. These challenges include: the proximity to the care provider, the time required for help to arrive, the identification of the criticality of the emergency, the appropriate level of care provided, the variances in training of emergency medical dispatcher personnel, and limited nature of emergency care resources. This invention addresses these challenges by providing consistent and proven advice and instruction for persons on the scene with choking patients. This invention, in its best mode of operation, operates as part of a system for the management, processing and response of an emergency medical dispatch system. This emergency medical dispatch system accomplishes the above objectives by: First, gathering necessary medical complaint information from emergency medical inquiry callers and providing emergency verbal instructions to individuals at the scene. Second, prioritizing the complaint to determine the criticality of the emergency. Third, assisting dispatched responders to be prepared for each emergency situation. Fourth, advising those on the way to provide care at the scene of specific problems or potential hazards. When used correctly this invention decreases the effective response time, while increasing the professionalism and control of emergency medical dispatchers, increases the accuracy and appropriateness of patient interrogation and well as the quality of gathered information, reduces the number of multiple unit responses thereby reducing the risk of emergency medical vehicular collisions, improves patient care, reduces burn-out and stress of dispatchers by improving their quality of training, decreases the risk of responder injury or mistake by providing responders with improved knowledge of the situation, provides an means for continuously improving the quality of emergency patient care, and provides a "zero-time" emergency medical response through guidance given remotely, typically over a telephone, to individual at the scene.

While being included within a greater invention that addresses all of the above issues, this invention specifically addresses the method or process of giving emergency medical counsel to choking patients and/or those individuals at the scene with the patient. Choking is a critical medical condition where rapid correct response is essential to the successful treatment of the patient. This invention is especially important since the travel time for an emergency medical team to the patient is often to long for the team to be able to give the most effective treatment. This invention provides a means for communicating, in an orderly manner, to individuals at the scene the information necessary to help them revive the patient. Accurate, efficient and systematic responses to calls for help with medical choking situations can and does make the difference in the successful resolution of such incidents.

2. Description of Related Art

It is desirable to provide a systematic and standardized method for responding to emergency medical requests, especially where the patient is suffering from choking and where individuals at the scene can be properly instructed help the patient. Although in the related art some attempt has been made to address the problem of medical care assessment, the related art does not address the specific problems of emergency dispatcher response to medical problems related to choking. Rather related art approaches describe the following. A process of helping patients assess their health, select appropriate health care, and guide such patients to an appropriate level and type of care. An automated medical history taking system and a technique wherein selected branch paths through a question repertory are provided. A method and apparatus for coordinating the actions of two or more medical teams, especially for instructional purposes. An expert system for providing suggested treatments for a patient with physical trauma. A medical payment system that incorporates computer technology in the storage, retrieval and processing of patient data and insurance claims. A knowledge base containing medical/pathological information on various diseases. A hospital computerized system for entering information pertinent to a patient's stay in the hospital. An expert computer system for processing medical claims. An interactive computerized apparatus and method for presenting medical information for diagnosis and study of disease. An automated and interactive positive motivation system to send a series of motivational messages and/or questions to a client to change or reinforce a specific behavioral problem. An artificial intelligent expert system. A rapid response health care communications system for providing rapid and reliable health services to patients located within or outside a health care facility.

For general background material, the reader is directed to U.S. Pat. Nos. 4,130,881, 4,237,344, 4,489,387, 4,839,822, 4,858,121, 4,945,476, 5,063,522, 5,065,315, 5,072,383, 5,253,164, 5,255,187, 5,471,382, and 5,596,994. Each of the above references is hereby incorporated by reference in its entirety for the material disclosed therein.

SUMMARY OF THE INVENTION

It is desirable to provide a system for emergency medical dispatch of health care services that provides the dispatcher a systematic method of interrogation of callers, where inquiries and instructions are pre-scripted, thus eliminating the variability due to different skills of the individual dispatchers and the need for the dispatcher to attempt to recall the appropriate inquiries and instructions each time a call is received. Furthermore, it is desirable to provide a system for emergency medical care dispatch that improves the accuracy and appropriateness of patient interrogation and resulting response generation. Such a system can formalize the roll of the emergency medical dispatcher as part of the professional chain of patient care. It is also desirable to have a method for communicating with medical response teams such that multiple unit and light-and-siren responses are reduced, thereby reducing the collision risks to emergency vehicles and preserving the limited emergency response resources. It is desirable to provide a medical dispatch system that improves patient care by improving the accuracy and usefulness of gathered information, thereby reserving paramedic teams for the most critical emergencies. It is desirable to have a medical dispatch system that reduces dispatcher burn-out and stress by improving information relayed to field responders while simultaneously providing such responders with increased safety awareness and knowledge of the field situation. Furthermore, it is desirable to have an emergency medical dispatch system that includes provisions for instructing, counseling, advising those on the scene in procedures and techniques that can aid in reviving an choking patient. It is desirable to have such provisions which incorporate proven techniques for guiding an on-scene individual through the process and which includes a scripted procedure which steps the dispatcher through the process without depending solely on the individual skills and knowledge base of the dispatcher.

Accordingly, it is the primary object of this invention to provide a medical dispatch system that is designed to guide the medical dispatcher through the interrogation, obtaining vital patient information regarding calls concerning patients who are choking.

Another object of this invention is to provide a cross-referenced scripted set of instructions to be given by the dispatcher to the caller in an patient choking medical emergency situation.

A further object of this invention is to improve the quality, efficiency and usefulness of the information received to and communicated by emergency medical dispatchers thereby improving the quality of emergency medical services provided to patient before, during and after the arrival of emergency medical technicians.

These and other objects of this invention, which will be clear to those of ordinary skill in the art upon review of this patent specification and claims, are achieved by an invention which permits a systematic gathering of patient information, with a set of scripted instructions and with guidance for relaying information to the field emergency personnel. The method and system of this invention is currently envisioned in two equally preferred embodiments. First, a set of cross referenced cards with scripted questions, instructions and categorizations is provided. Second, a computerized process is provided with software controlling the access and reference points to a computerized database of emergency medical inquiries and instructions is provides. Each preferred embodiment incorporates the same essential method of this invention, though each has its own particular advantages.

DETAILED DESCRIPTION OF THE INVENTION

This invention provides a method, system and an apparatus for receiving, processing and communicating emergency medical information, specifically related to communicating instructions to individuals at the scene for the emergency treatment of choking victim patients. When the invention is properly employed the initial interrogation of the caller or patient will have previously provided the emergency medical dispatcher critical patient information which has indicated that the patient is most likely choking. This information has been applied in protocols which have led the dispatcher through a scripted interrogation, gathering additional related information, and categorizing the problem by assigning a determinant value establishing the criticality of the problem. This invention then functions by providing appropriate scripted established emergency medical instruction to the individuals on the scene.

Figure 1:
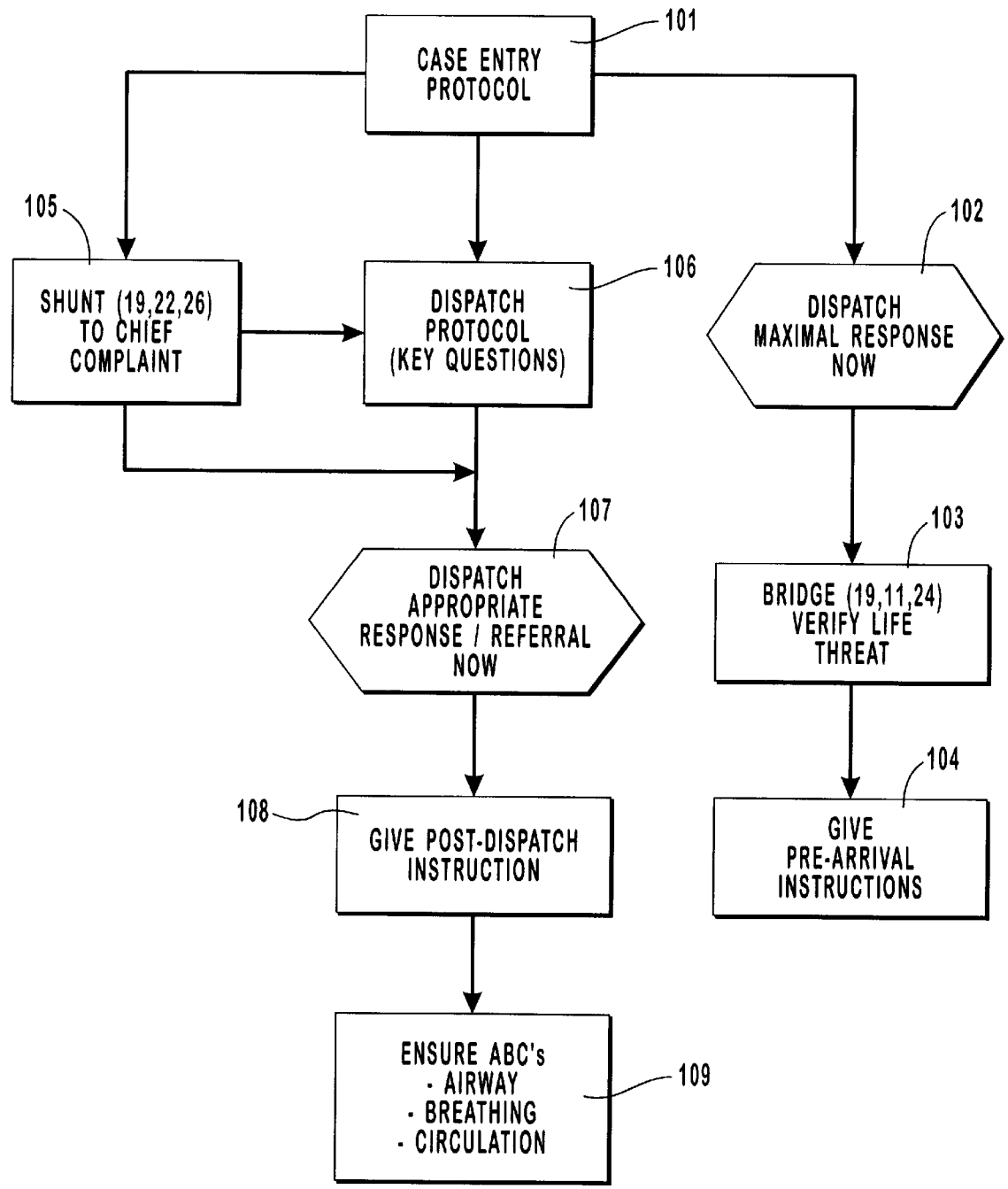
FIG. 1 depicts the principle elements of the complete system in which the preferred embodiment of the invention operates and the relationship of the elements of system to each other, and serves to put this invention in the context of the complete system.

FIG. 1 shows the complete system in which the invention operates in its best mode. The process of managing emergency medical dispatchers, the information they require and the information they give is detailed in FIG. 1. The case entry protocol 101 provides the initial steps through which the all emergency callers or patients are taken to provide symptom information and to access medical information. The purpose of the case entry protocol 101 is to receive sufficient information to permit the dispatcher to identify the caller's chief complaint. This critical information received during the primary interrogation 101 includes a description of the problem (or the patient's complaint), the patient's age and the status of consciousness and breathing. This information is also referred to as "the four commandments of emergency medical dispatching." If the dispatcher receives information that the patient is unconscious and not breathing (or unconscious and breathing is uncertain or conscious but not breathing where the failure to breath has been verified), for whatever reason, a maximal response 102 is sent immediately, before continuing with any further interrogation or instructions, and the caller is told to stay on the line for further instructions. A maximum response dispatch 102 may include such resources as emergency medical technicians, ambulances, paramedics, and other appropriate medical care givers. The life threat is then verified 103 and pre-arrival instructions are given 104. These pre-arrival instructions 104 include six treatment sequence scripts covering Arrest, Choking, and Childbirth. The pre-arrival instruction procedure for choking is the heart of this invention. Instructions 104 are given to guide the caller through CPR, the Heimlich Maneuver, or emergency childbirth procedures. In many cases, the result of properly conveyed instructions is a more viable patient by the time field personnel arrive. Should the dispatcher learn that the patient is breathing, but the dispatcher lacks sufficient information to directly go to the Key Questions of the Dispatch Protocol 106, the dispatcher is shunted 105 to additional interrogations whose purpose is to give the dispatcher the necessary information to ascertain the caller's chief complaint while focusing on heart problems, industrial/machinery accidents and/or general sick person issues. Once the dispatcher has enough information to have identified the caller's chief complaint, the dispatcher is taken to the Dispatch Protocol 106 where additional interrogations are performed to complete "key questions." This secondary interrogation 106 typically takes approximately 30 seconds and tends to focus on the specific or chief complaint of the caller. This secondary interrogation, or Dispatch Protocol 106, provides a more orderly and closer view of the patient so that the pre-hospital care provided is appropriate and in keeping with the severity of the injury or illness. During this step 106 the dispatcher will match the symptoms, or combination of symptoms, discovered through interrogation and send the appropriate response 107. The appropriate response 107 is determined through a system of assigning determinant levels and numbers, from A2 generally less serious to D1 generally very serious. When the dispatcher identifies a determinant in one of the four levels (Alpha-A, Bravo-B, Charlie-C, and Delta-D) the response configuration (emergency vehicles and the mode of response) is dispatched as indicated by the response protocol. After the responders (field emergency medical care-givers) has been sent, the dispatcher remains on the telephone with the caller to give instructions 108 regarding what to do, and what not to do, prior to the arrival of the responders. This information is taken from the "Post-Dispatch Instructions" section of the protocols and provided whenever possible and appropriate. A main purpose of these "Post-Dispatch Instructions" 108 is to prepare the patient for and to expedite the field personnel's work at the scene. "Post-Dispatch Instructions" include such instructions as to collect the patient's medications, write down the name of the family doctor and put away pets. Each caller is also instructed to ensure 109 that the patient has an open airway, is breathing, is given nothing to eat or drink before responders arrive and, if necessary, how to treat for shock using the procedure given in the reference script for Airway, Breathing, and Circulation. Callers are routinely advised to "call back if the patient's condition worsens for further instructions."

Figure 2:
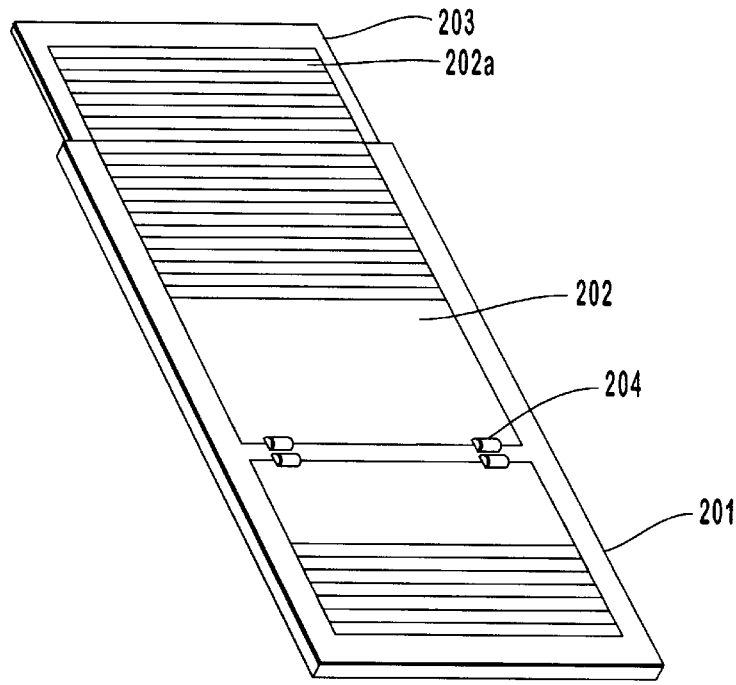
FIG. 2 depicts the flip card apparatus showing a preferred embodiment of the invention.

FIG. 2 depicts an embodiment of the flip card apparatus showing a preferred system for the use of the invention. One preferred embodiment of the invention involves the use of a flip card apparatus 201. The flip card apparatus 201 has the advantage of organizing the cards 202 so that the top or bottom, label edge of each card can be seen by the user. Each card 202 is separately fastened into the apparatus with one or more fasteners 204. The steps embodying the elements of this invention, the entry protocol, are displayed on a top flap 203 and the first card 202*a*. Alternative embodiments of the card apparatus can be a deck of cards bound in a manner well known to those skilled in the art. In the current embodiment of the flip card apparatus there are sixty-four chief complaint cards, twelve pre-arrival instruction cards, two post-dispatch cards, one determinant classification card and two entry protocol cards. The cards are generally organized in pairs, with the top card providing the protocol questions, instructions, jump directions and determinant assignments. The bottom card provides information the dispatcher uses to improve the dispatcher's decision making process.

Figure 3:
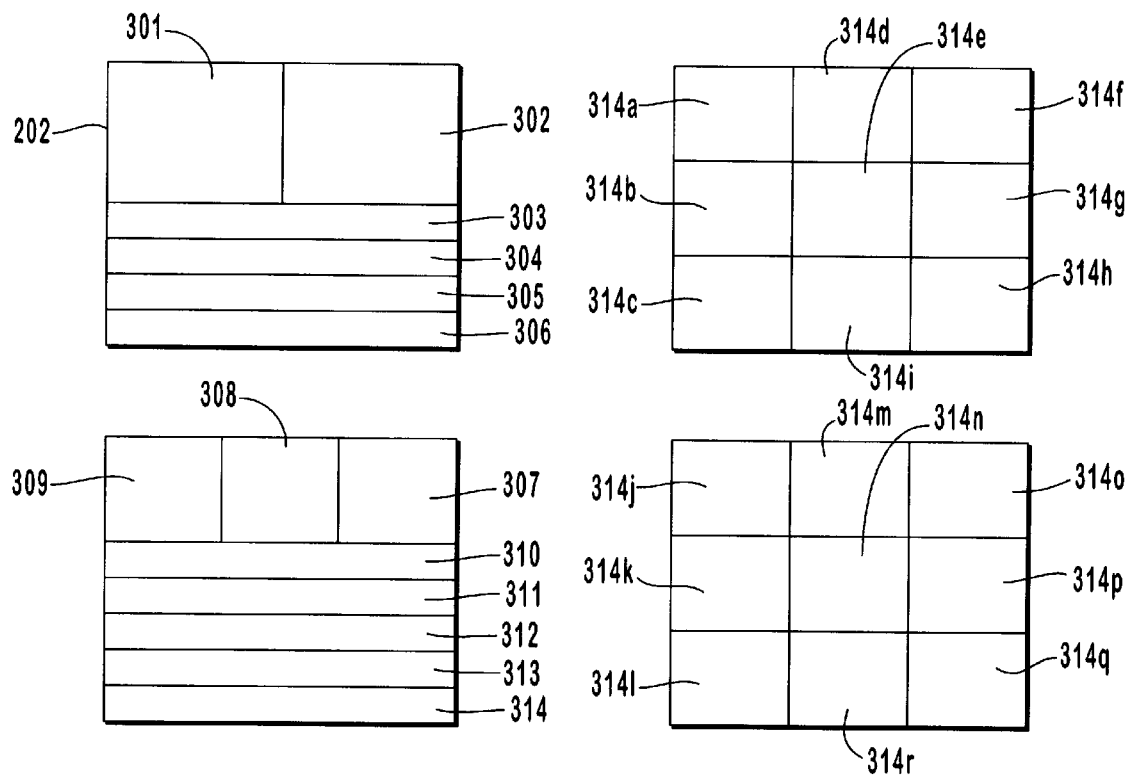
FIG. 3 shows a view of the sections of a typical flip card as used in the flip card apparatus embodiment of the invention.

FIG. 3 shows a view of the sections of a typical flip card, as used in the flip card apparatus embodiment of the invention. The typical flip card 202 is divided into logical sections for ease of use and consistency. A key question section 301 is provided as a script to the dispatchers to ensure that all key questions are asked in a calm, consistent, systematic manner. After all key questions are asked from the key question section 301, typically the dispatcher determines the appropriate determinant level. Sections A-Alpha 303, B-Bravo 304, C-Charlie 305 and D-Delta 306 are provided to aid the dispatcher in making the determinant designation. Each determinant level may have one or more sublevels. Generally, the most critical call is given a determinant level of D-Delta and the least critical call is given a determinant level of A-Alpha. The more critical the determinant level assigned to a call, the more medical resources and urgency may be applied to provide help. For example, an A-Alpha call will typically be responded to by emergency medical technicians and an ambulance proceeding to the patient under the safest method reasonably possible, while a D-Delta call will typically be responded to by the closest emergency medical technicians, an ambulance, paramedics, all who will proceed under the most urgent method possible. Sublevels may not indicate the criticality of the call, rather sublevel designations indicate the type of call, information often especially important to the dispatched medical team. After the determinant code is determined 303–306 the dispatcher is referred to the post-dispatch instructions section 302. The purpose of the post-dispatch instructions is to systematically prepare for and expedite the field personnel's job at the scene and to prevent further harm to the patient or others at the scene. The post-dispatch instruction section 302 includes such instructions as collecting the patient's medications, writing down the name of the family doctor and securing animals in the area. Each caller is also instructed, from the post-dispatch instruction section 302, to ensure that the patient has an open airway, is breathing, is given nothing to eat or drink before responders arrive, and, if needed, how to treat for shock using a reference script. Callers are also routinely advised to "call back if the patient's condition worsens for further instructions." Pre-arrival instructions 106 are provided on alternative cards 314, subsectioned as shown in FIG. 3 as 314 *a–r*. These pre-arrival instruction sections 314 provide scripted treatment sequences for arrest, choking and childbirth. These procedures, provided through sections 314, guide the caller through CPR, the Heimlich Maneuver or emergency childbirth procedures. Sections 307 to 314 provide important information to the dispatcher for the dispatcher's use in providing more educated responses. This information includes such information as categorizations of dangerous areas or injuries; types of injuries; symptoms; rules and axioms. Such information as is systematically provided to place the key questions of section 301, the determinant classifications of sections 303–306, and the post-dispatch instructions of section 302 into context for the dispatcher.

Figure 4:
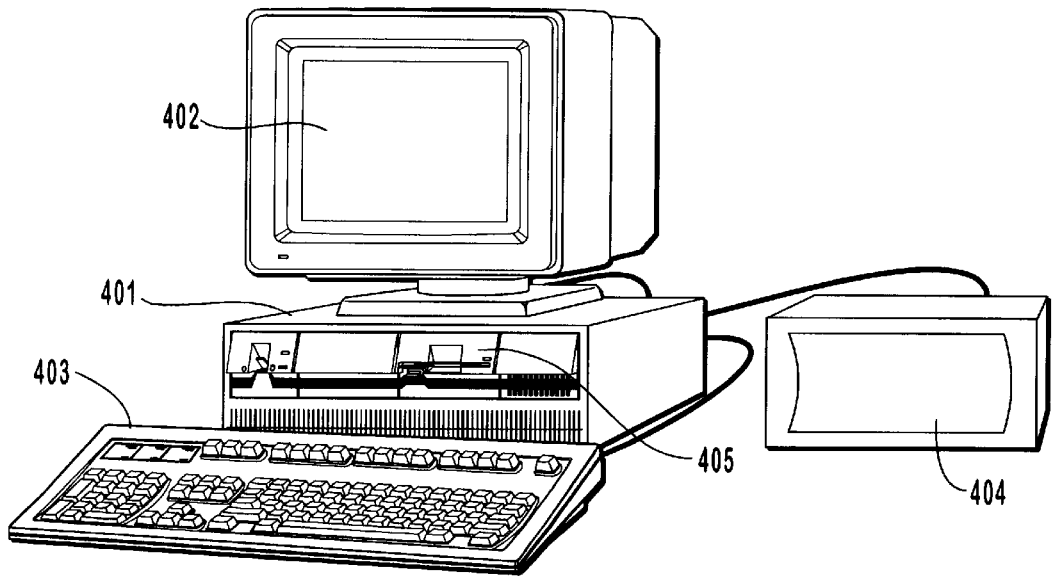
FIG. 4 shows a system diagram showing the components of a typical computer system used in the computerized embodiment of the invention.

FIG. 4 shows a system diagram of the components of a typical computer system used in the computerized embodiment of the invention. A second preferred embodiment of the invention is designed to operate in combination with a computer system using specially designed computer software incorporating the procedure of the invention. A typical computer system used in combination with software incorporating the invention includes a processing unit 401 to execute the instructions of the software; a display unit 402 to provide the means for providing the dispatcher with the prompts and information necessary to practice the invention; an input device 403 to provide the means for the dispatcher to interact with the software version of the invention; a storage device 405 for storage of the software and the files associated with the invention; and an output device 404 for printing reports and other information.

Figure 5:
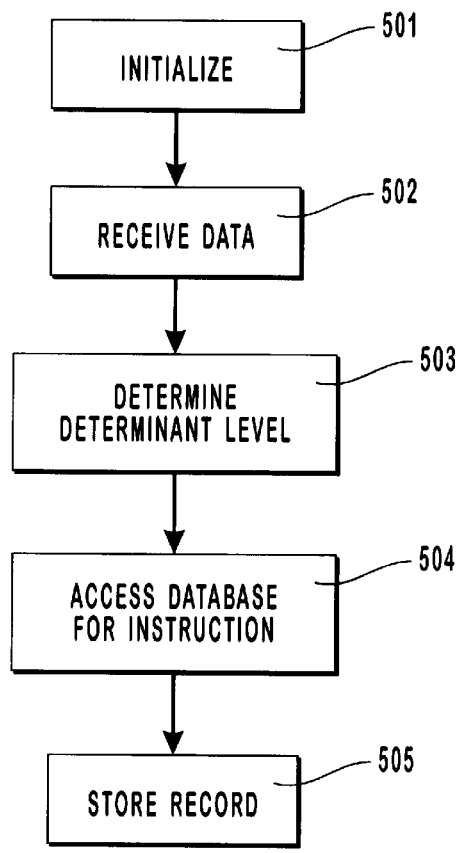
FIG. 5 shows a flow chart representation of the preferred top level steps of the invention.

FIG. 5 shows a process flow chart representation of the preferred top level steps of the invention. The software embodiment of the procedure of the invention is accomplished by performance of a number of procedural steps. First, the software is initialized 501. Data is received 502 following the request for information from the caller. As data is received 502, the determinant level is determined 503. Intermediate determinant levels are produced as information is received and processed, the final determinant level is only achieved after all necessary information is received and processed. A data base is accessed 504 to produce the appropriate instructions for communication with the caller. Records of the calls and queries are stored 505, for historical reports, for review of the dispatchers and for continued quality assurance control.

Figure 6:
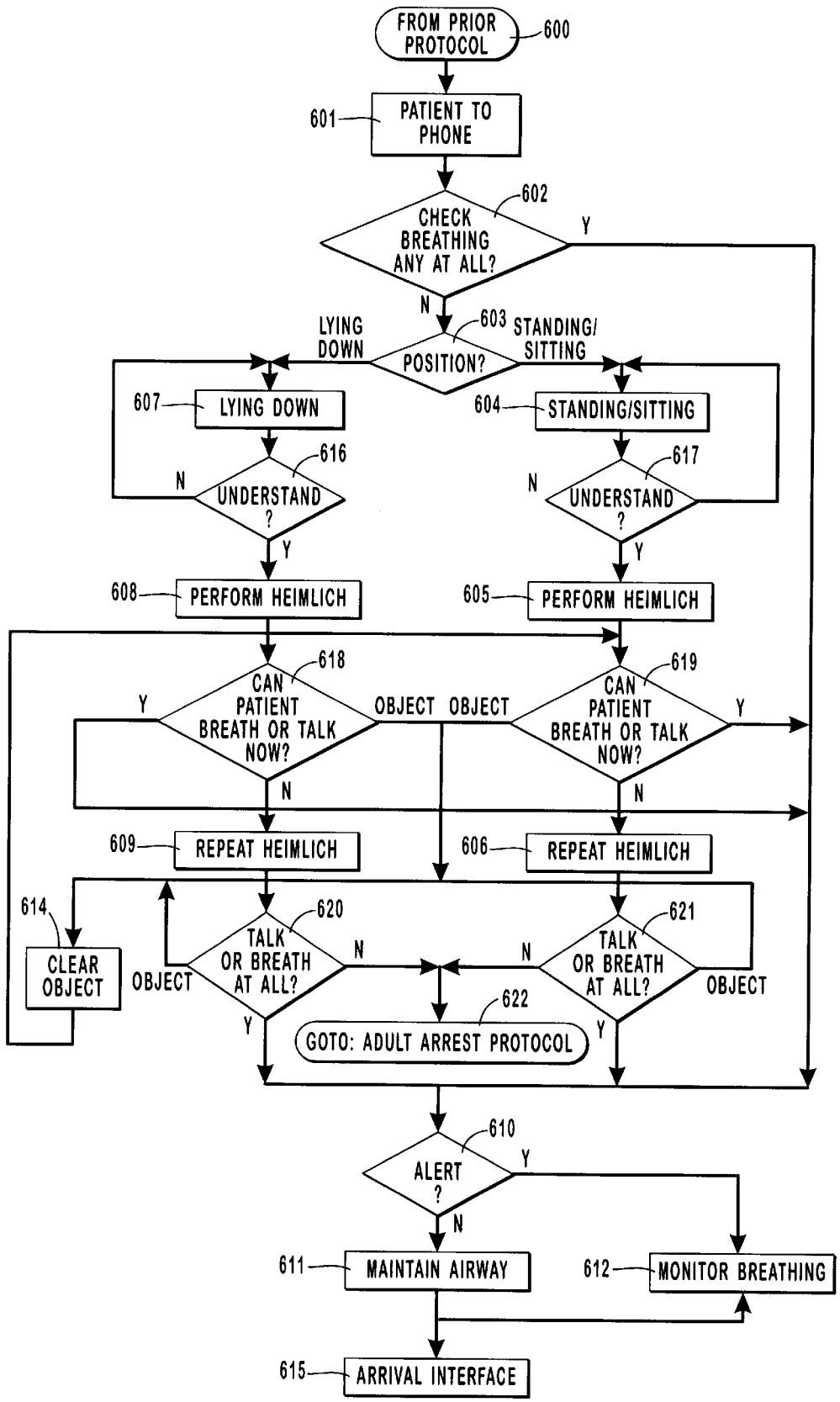
FIG. 6 depicts the detailed steps of the choking pre-arrival instructions protocol process for adults, constituting the preferred embodiment of the invention for these patients.

FIG. 6 depicts the detailed steps of the choking pre-arrival instruction protocol for adults, in a form reflecting the preferred embodiment of the invention. A similar, functionally identical protocol is also provided for infants and children. The only significant change is in the numbering of the steps. Although the following steps of the protocol process of the invention need not necessarily be accomplished in this specific order, alternative ordering of the steps of the invention are possible, this order of the steps of the process has been determined by the inventor to be the best mode of the invention. First, this protocol of pre-arrival instructions for choking adults is reached, in the best mode of the invention, after the dispatcher has interrogated the caller, determined the type of medical emergency, assigned a determinant value describing the level of emergency and, in general, after the dispatcher has dispatched an emergency medical response team to the site of the arrest emergency. The following procedure of this invention is performed as a systematic means of providing interim emergency medical instruction to individuals at the scene. Therefore, this invention is generally reached from a prior emergency medical protocol 600. After each step the caller is instructed to "Do it now and then come right back to the phone." The caller is instructed to bring the patient as close to the phone as possible 601. During this step the caller is also informed that he or she is going to be instructed on how to do the Heimlich maneuver, and not to hang up. The caller is asked where the victim is now. Next the caller is instructed to perform the check breathing step 602, by looking very carefully at the victim to see if he or she is breathing at all. Do it now and come back to the phone to report. If the victim is breathing, the caller is instructed to check if the victim is alert 610.

If the victim is not breathing, the caller is asked whether the victim is standing/sitting or lying down 603. If the victim is standing or sitting, then the caller is instructed to perform the standing/sitting step 604. This step involves telling the caller to stand behind the victim, putting the caller's arms around the victims waist. The caller is told to make a fist and grasp it with the other hand. Placing the thumb of the caller's fist in the stomach just above the belly button, being sure to stay below the ribs and the breast bone. The caller is then asked if he or she understands the dispatcher's instructions 617. If the caller doesn't understand, the dispatcher repeats the instructions. If the caller does understand, then the caller is instructed to perform the Heimlich maneuver 605, by in one quick motion, jerking hard, inward and up into the stomach. Doing this five times and then checking the victims mouth for an object. The dispatcher then asks if the victim can breath or talk now 619. If so, the caller checks the alertness of the victim. If not, the caller is instructed to repeat the Heimlich maneuver 606. Again, the caller is asked to check if the victim can breath or talk at all now 621. If the victim still cannot breath or talk, the dispatcher goes to the Adult Arrest Protocol for further instructions 622

If the victim is lying down the caller is instructed to perform the lying down step 607. This step involves telling the caller to make certain that the victim is lying face up. The caller is instructed to straddle the victim's hips with the caller's legs, placing the caller's hands, one on top of the other, on the victim's stomach just above his or her belly button. The caller is then asked if he or she understand the dispatcher's instructions 616. If the caller doesn't understand, the dispatcher repeats the instructions. If the caller does understand, then the caller is instructed to perform the Heimlich maneuver 608, by with a quick, downward thrust, push, using your weight into his or her stomach. Do this five times then check the victims mouth for an object. The dispatcher then asks the caller if the victim can talk or breathe now 618. If an object is obstructing the victim's breathing, the clear object step 614 is performed. If the victim still cannot breath the Heimlich maneuver is repeated 609. Again the caller is asked if the victim can talk or breathe at all now 620. If the victim still cannot breathe then the dispatcher goes to the Adult Arrest Protocol 622 for further instructions. If the victim can breathe the caller is asked if the victim is alert 610.

If an object has been released, it should be cleared from the victims mouth 614. If the victim can talk or breathe, the caller is instructed to determine if the victim is alert 610. If the victim is now alert, then the caller is instructed to monitor the victims breathing 612. If the victim is not alert, the caller is instructed to maintain the victims airway 611, by keeping his or her head tilted back and watching him or her very closely to be sure that the victim is breathing all right. Lastly, the caller is instructed to perform the arrival interface step of the invention 615 by not leaving the victim alone when you hear the paramedics arrive, and when they arrive hand the phone to one of the paramedics (EMT's). Check that the door is unlocked and if possible have someone to open the door up.

Figure 7:
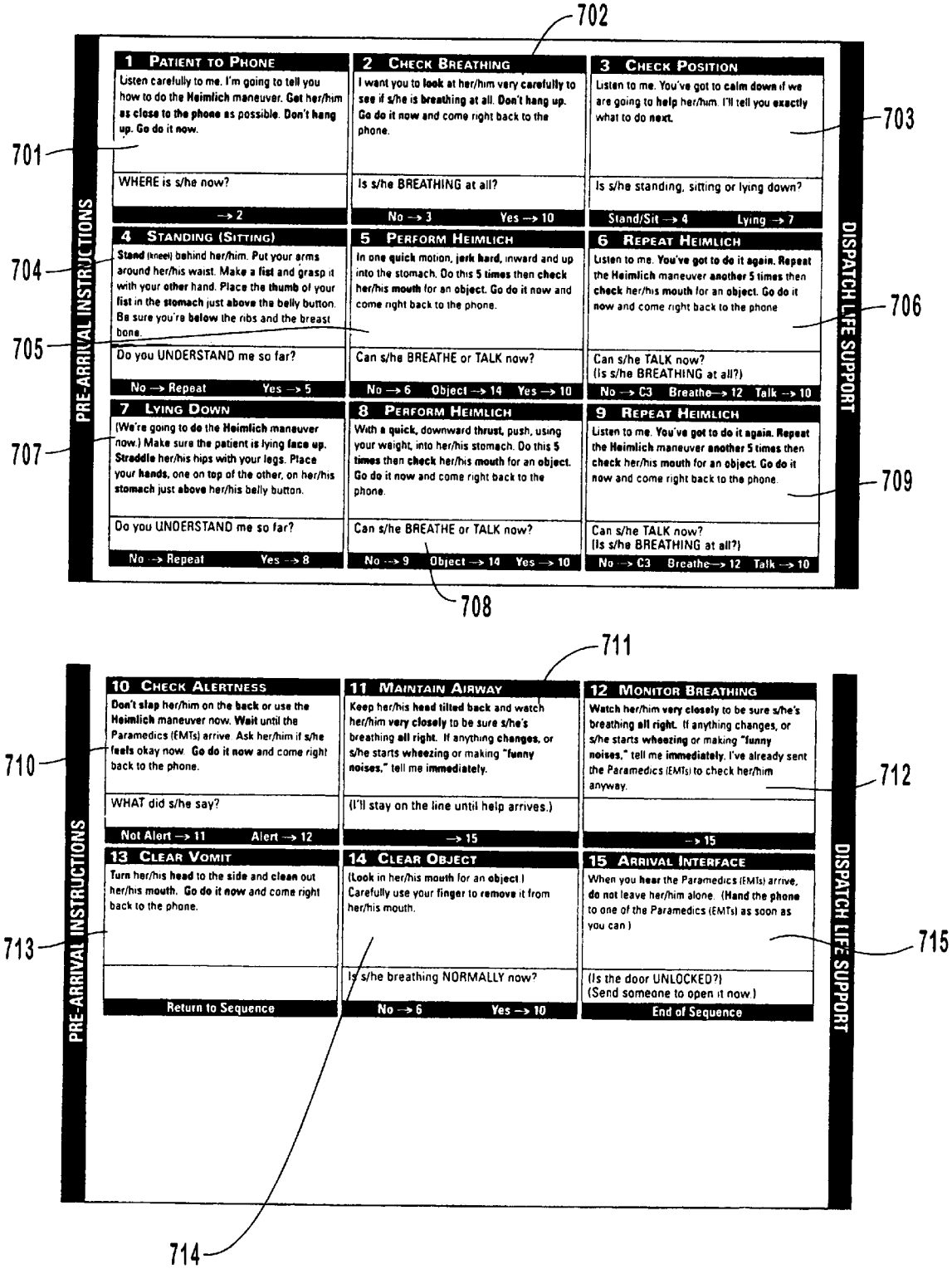
FIG. 7 shows the steps of the choking adult pre-arrival instructions protocol of the flip card deck embodiment of the invention.
Figure 8A:
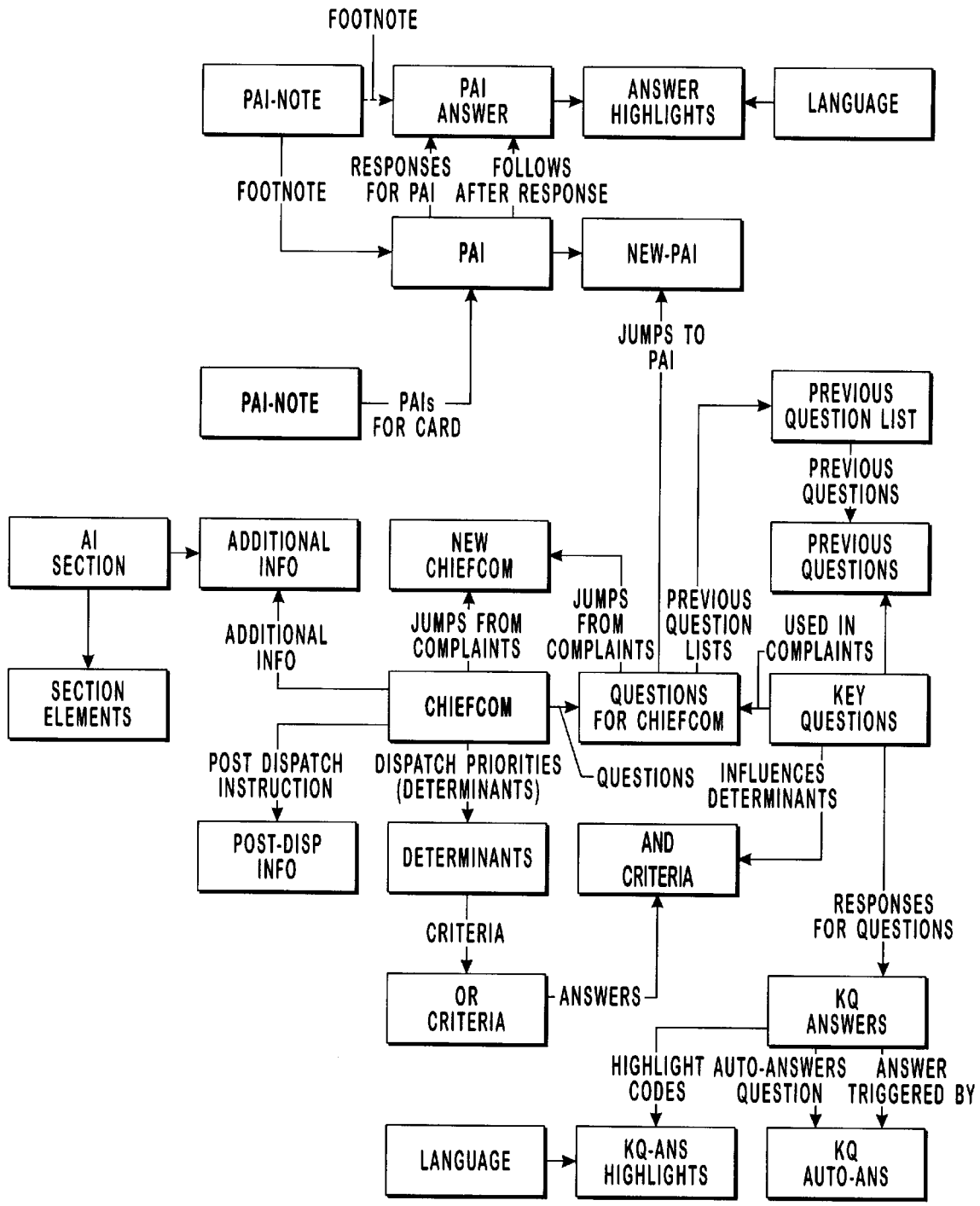
Figure 8B:
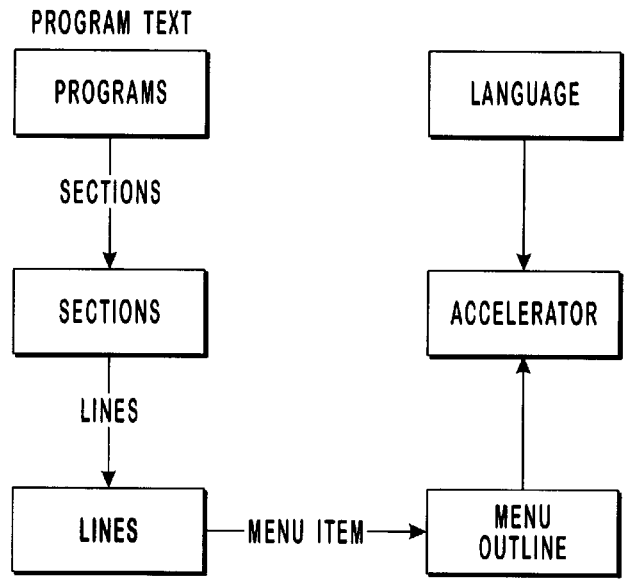
Figure 8C:
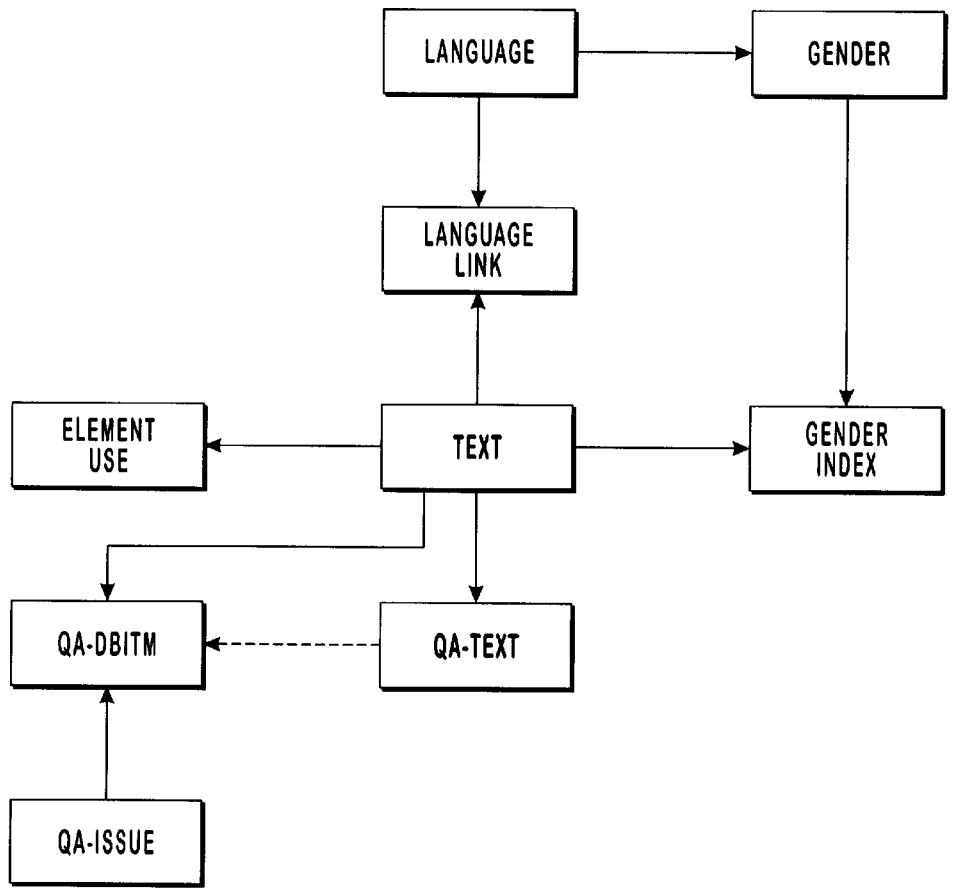
Figure 8D:
Figure 8E:
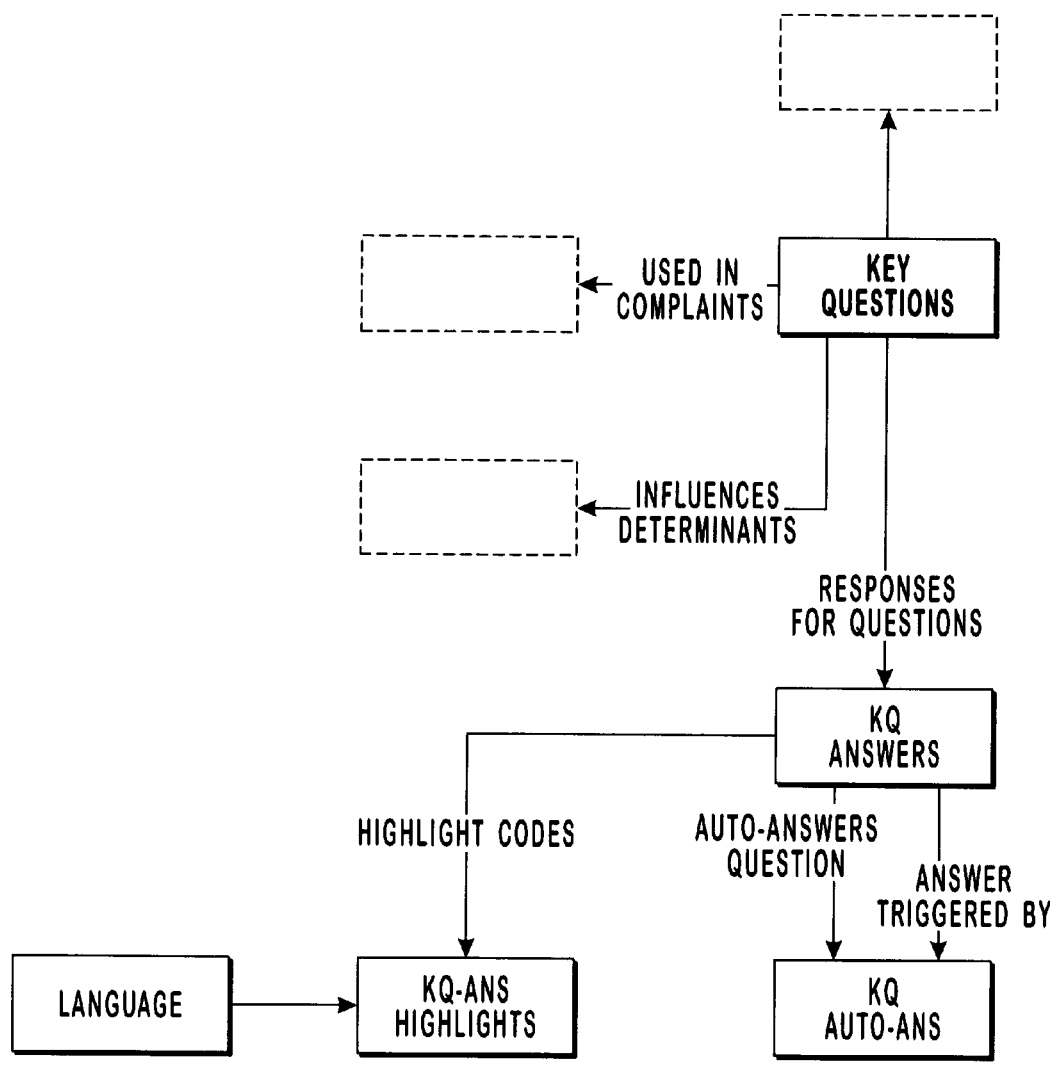
Figure 8F:
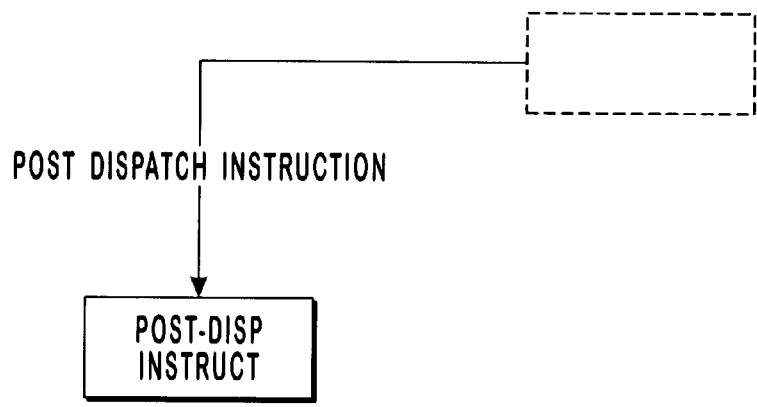
Figure 8G:
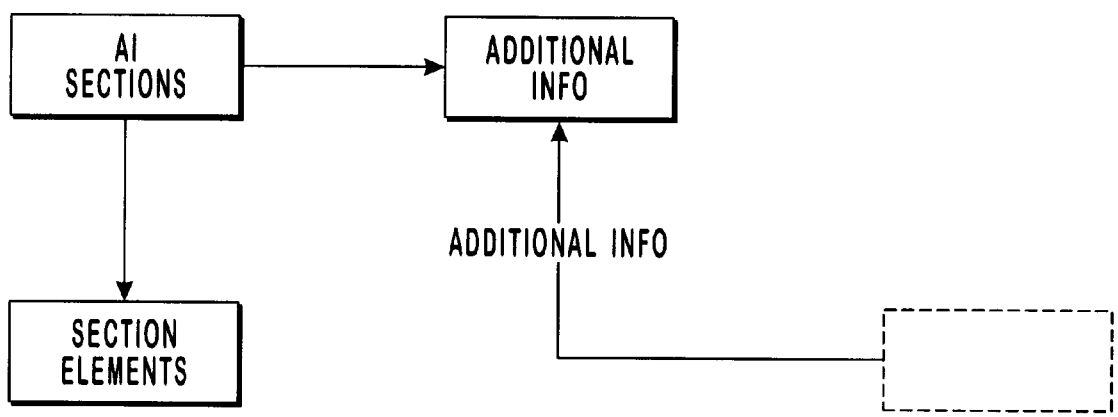
Figure 8H:
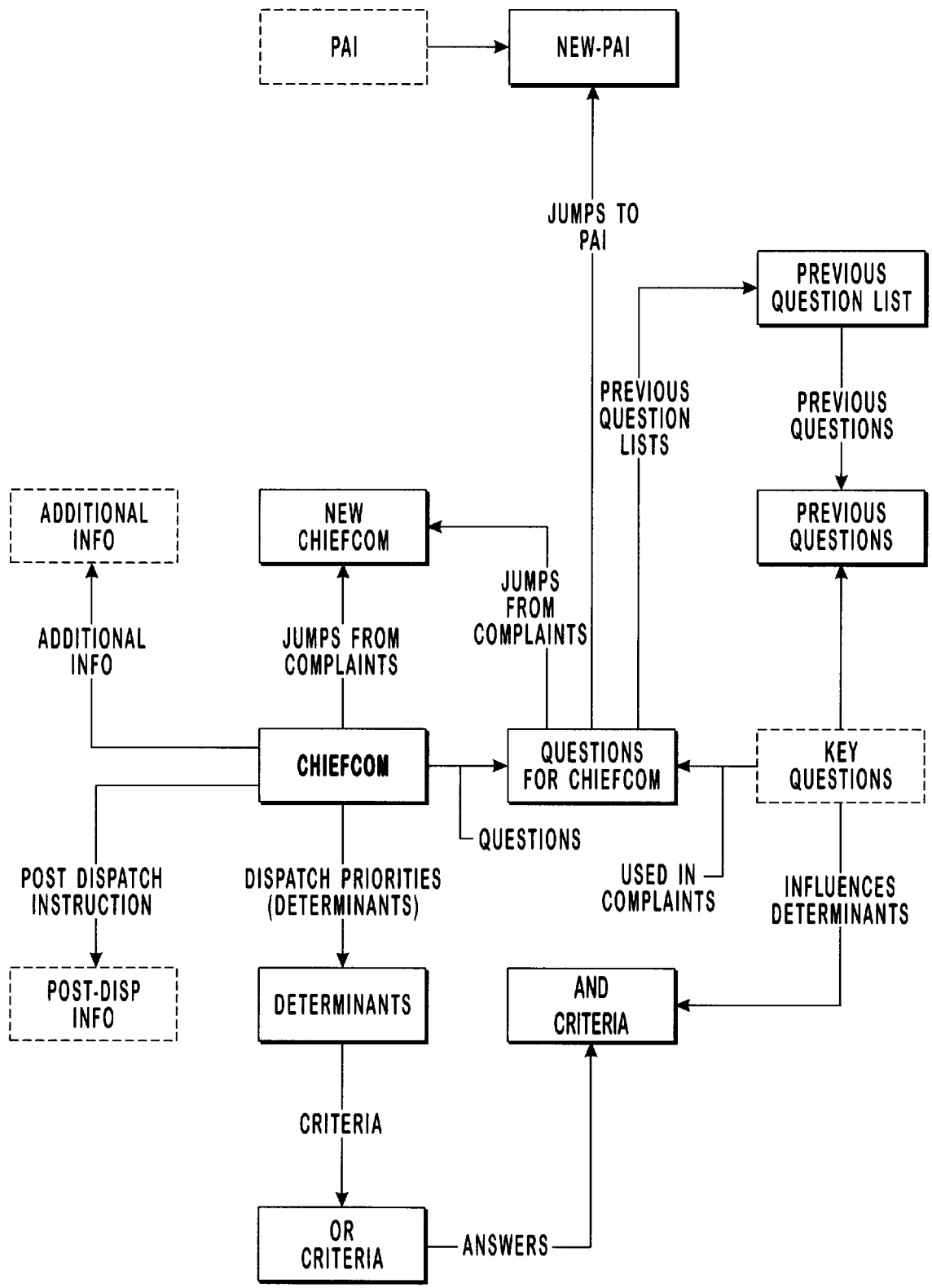

FIG. 7 depicts the preferred embodiment of the flip cards showing the steps of the choking—adult instruction protocol invention. Functionally equivalent flip cards are also provided in the best mode of the invention for the choking infant/child protocol invention. The patient to phone step is shown 701. The check breathing step is shown 702. The check position step is shown 703. The standing/sitting step is shown 704. The perform Heimlich step is shown 705. The repeat Heimlich step is shown 706. The lying down step is shown 707. The perform Heimlich step is shown 708. The repeat Heimlich step is shown 709. The check alertness step is shown 710. The maintain airway step is shown 711. The monitor breathing step is shown 712. The clear vomit step is shown 713. The clear object step is shown 714. The arrival interface step is shown 715.

It is to be understood that the above-described embodiments are merely illustrative of numerous and varied other embodiments which may constitute applications of the principles of the invention. Such other embodiments may be readily devised by those skilled in the art without departing from the spirit or scope of this invention and it is our intent that they be deemed within the scope of our invention.

Appendix of Computer Software

METHOD AND SYSTEM FOR GIVING REMOTE EMERGENCY MEDICAL

COUNSEL TO CHOKING PATIENTS

Inventors:     Jeffrey J. Clawson

Assignee:     Medical Priority Consultants, Inc.

Address:      139 E. South Temple, Suite 500

Salt Lake City, Utah 84111

ProQA method of determining the list of chief complaints to present to the user for selection Within ProQA, during the initial case entry, the user is allowed to enter one of three values for the patient's state of consciousness and one of four values for their breathing status. Based on these two parameters, one of four possible lists should be displayed to limit the user's selection of the final data entry field.

The following is a truth table for the input and output values of the formula:

| Conscious | Breathing | Chief Complaint list |
| --- | --- | --- |
| No | Yes | 31, 9, 11, 12, 13, 14, 15, 23, any other card |
| No | No | 9, 11, 14, 15, any other card |
| No | Unknown | 9, 11, 14, 15, any other card |
| No | Uncertain | 9, 11, 14, 15, any other card |
| Yes | Yes | Any card |
| Yes | No | 11 |
| Yes | Unknown | Any card |
| Yes | Uncertain | 11 |
| Unknown | Yes | Any card |
| Unknown | No | 9, 11, 14, 15, any other card |
| Unknown | Unknown | Any card |
| Unknown | Uncertain | 9, 11, 14, 15, any other card |

The following is a function, written in the C programming language (copyright 1996 by Medical Priority Consultants, Inc.), that implements the above table.

```c
// Input values for conscious parameter
#define CONS_NO    0
#define CONS_YES   1
#define CONS_UNK   2

// Input values for breathing parameter
#define BRTH_NO    0
#define BRTH_YES   1
#define BRTH_UNK   2
#define BRTH_UNC   3

// Output values for valid_cc function
#define CCS_ALL    0   // Choice of chief complaints: any
#define CCS_HPLUS  1   // Choice of chief complaints: 31, 9, 11, 12, 13, 14, 15, 23, any other
#define CCS_HEART  2   // Choice of chief complaints: 9, 11, 14, 15, any other
#define CCS_CHOK   3   // Choice of chief complaints: 11

// Determine the chief complaint codes valid for the conscious and breathing responses entered
int valid_cc(int conscious, int breathing)
{
    switch (conscious)
    {
    case CONS_NO:
        switch (breathing)
        {
            case BRTH_YES:   return (CCS_HPLUS);

case BRTH_NO:
            case BRTH_UNK:
            case BRTH_UNC:   return (CCS_HEART);
        }
        break;
    case CONS_YES:
        switch (breathing)
        {
            case BRTH_YES:
            case BRTH_UNK:   return (CCS_ALL);

case BRTH_UNC:
            case BRTH_NO:    return (CCS_CHOK);
        }
        break;
    case CONS_UNK:
        switch (breathing)
        {
            case BRTH_YES:
            case BRTH_UNK:   return (CCS_ALL);

case BRTH_NO:
            case BRTH_UNC:   return (CCS_HEART);
        }
        break;
    }
    return (CCS_ALL);
}
```

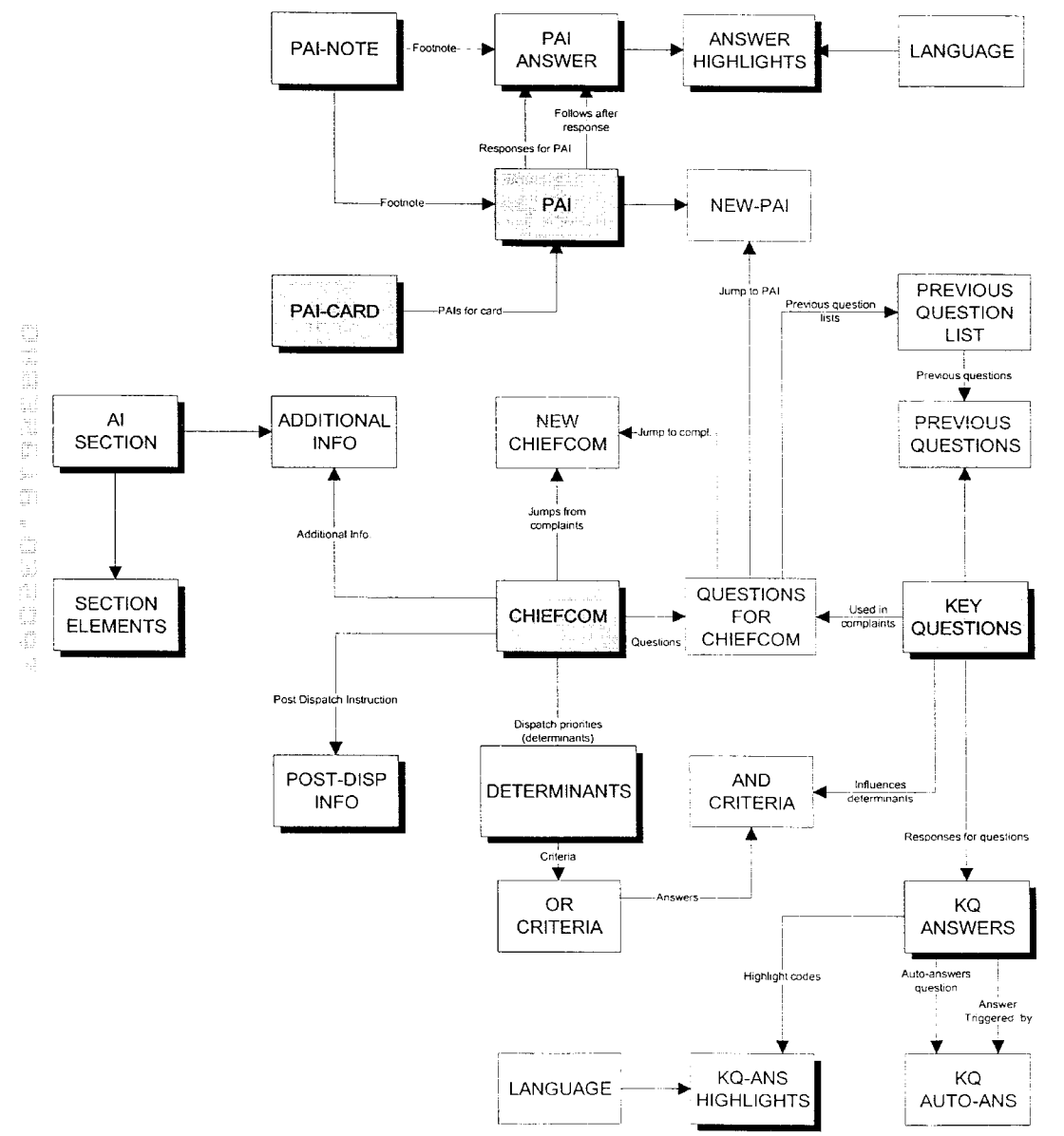
*Protocol Table Relationships*

I claim:

1. A method for giving remote emergency medical counsel to choking victims, comprising the steps of:

(A) providing instructions to an emergency medical dispatcher, including instructions to inquire for specific information, including inquiring if the victim can breathe; inquiring if the victim can talk; and inquiring if the victim is alert, to receive response information, and to use said response information to determine a degree of criticality, wherein said determined degree of criticality is used by said emergency medical dispatcher to appropriately dispatch an emergency medical response, and dispatching said emergency medical response to the victim;

(B) inquiring if the victim can breathe now;

(C) inquiring if an object is obstructing the breathing of the victim, and if an object is obstructing the breathing of the victim providing an instruction on clearing the object and testing again if the victim can breathe now;

(D) instructing that if said discovered object is cleared and still the victim cannot breathe, to maintain the victim's airway; and (E) giving remote emergency medical counsel by providing instructions for performing the Heimlich maneuver.

2. A system for managing the process of responding to related medical injuries relating to choking victims, the system comprising:

(A) a set of instructions for use by an emergency medical dispatcher, including instructions to inquire for specific information, including inquiring if the victim can breathe; inquiring if the victim can talk; and inquiring if the victim is alert, to receive response information, and to use said response information to determine a degree of criticality, wherein said determined degree of criticality is used by said emergency medical dispatcher to appropriately dispatch an emergency medical response, and to dispatch said emergency medical response to the victim;

(B) a first inquiry as to whether the victim can breathe now;

(C) a second inquiry as to whether an object is obstructing the victim's breathing, and if an object is obstructing the breathing of the victim an instruction on clearing the object and testing again if the victim can breath now;

(D) a third inquiry as to whether said discovered object is cleared and if the victim cannot breathe, an instruction on maintaining the victim's airway; and (E) an instruction on performing the Heimlich maneuver.

3. A method for managing the process for responding to an emergency medical call relating to a choking victim in general purpose computer system comprising:

a central processing unit;
dynamic memory,
static memory,
a display device,
an input device,
an output device,
a mass storage device which contains
   a number of emergency medical instruction records,
   a number of medical information records,
   a grouping of determinant codes,
   a number of emergency medical inquiry reports,
the method comprising the steps of:

(A) displaying on said display device instructions to an emergency medical dispatcher, including instructions to inquire for specific information, said specific information including whether the victim can breathe, whether the victim can talk, and whether the victim is alert, to input into said general purpose computer using said input device responses to said inquiries, to process in said general purpose computer said input responses and compute a degree of criticality, wherein said degree of criticality is used to select an appropriate emergency medical response;

(B) receiving on said input device data indicating whether the victim can breathe now;

(C) displaying on said display device an instruction that if an object is discovered obstructing the breathing of the victim, to clear the object and to test again if the victim can breathe now;

(D) displaying on said display device an instruction that if said discovered object is cleared and still the victim cannot breathe, that the victim's airway is to be maintained; and (E) displaying on said display device instructions on performing the Heimlich maneuver.

4. A method for giving remote emergency medical counsel to choking victims, comprising the steps of:

(A) providing instructions to an emergency medical dispatcher, including instructions to inquire for specific information, including whether the victim can breathe, can talk or is alert, to receive response information, and to use such response information to generate a determinant of a degree of criticality, wherein said determinant of degree of criticality is used by said emergency medical dispatcher to dispatch an appropriate emergency medical response;

(B) inquiring whether the victim can breathe now;

(C) if an object is discovered obstructing the breathing of the victim, instructing on clearing the object and testing again if the victim can breathe now;

(D) if said discovered object is cleared and still the victim cannot breathe, instructing on maintaining the victim's airway; and (E) giving remote emergency medical counsel by providing instructions for giving chest thrusts.

* * * * *